United States Patent [19]
Clark et al.

[11] Patent Number: 6,096,272
[45] Date of Patent: Aug. 1, 2000

[54] AUTOMATED MICROBIOLOGICAL TESTING APPARATUS AND METHODS THEREFOR

[75] Inventors: Alexander W. Clark, Baltimore, Md.; Paul Gladnick, Seattle, Wash.; Robert E. Armstrong, Hunt Vally, Md.; Nicholas Bachur, Monkton, Md.; Klaus W. Berndt, Timonium, Md.; Dwight Livingston, Fallston, Md.

[73] Assignee: Becton Dickinson & Company, Franklin Lakes, N.J.

[21] Appl. No.: 09/083,130

[22] Filed: May 22, 1998

Related U.S. Application Data
[60] Provisional application No. 60/047,481, May 23, 1997.

[51] Int. Cl.⁷ .................................................. G01N 21/17
[52] U.S. Cl. ..................... 422/64; 435/287.3; 435/288.7; 422/67
[58] Field of Search .................... 422/64, 67; 435/287.3, 435/288.7

[56] References Cited

U.S. PATENT DOCUMENTS

| | | | |
|---|---|---|---|
| Re. 31,150 | 2/1983 | Ginsberg et al. | 422/64 |
| 3,932,131 | 1/1976 | Rolfe-Fontana | 422/64 X |
| 4,116,775 | 9/1978 | Charles et al. | 435/287.3 X |
| 4,118,280 | 10/1978 | Charles et al. | 435/287.3 |
| 4,406,547 | 9/1983 | Aihara | 422/64 X |
| 4,427,294 | 1/1984 | Nardo | 422/64 X |
| 4,456,380 | 6/1984 | Kondo et al. | |
| 4,536,369 | 8/1985 | Sakurada et al. | 422/64 X |
| 4,687,638 | 8/1987 | Benajam | 422/64 X |
| 4,724,215 | 2/1988 | Farber et al. | |
| 4,814,667 | 3/1989 | Tanaka | |
| 4,856,073 | 8/1989 | Farber et al. | |
| 4,896,963 | 1/1990 | Kato | 422/64 X |
| 5,003,611 | 3/1991 | Miyake et al. | |
| 5,079,144 | 1/1992 | Carr et al. | |
| 5,089,395 | 2/1992 | Snyder et al. | |
| 5,206,151 | 4/1993 | Robertson | |
| 5,290,701 | 3/1994 | Wilkins | |
| 5,320,808 | 6/1994 | Holen et al. | 422/64 |
| 5,340,747 | 8/1994 | Eden | |
| 5,501,959 | 3/1996 | Lancaster et al. | |
| 5,817,475 | 10/1998 | Gibbs et al. | |
| 5,853,666 | 12/1998 | Seaton et al. | 435/288.7 X |

FOREIGN PATENT DOCUMENTS

| | | |
|---|---|---|
| 0181228 | 5/1986 | European Pat. Off. |
| 0258565A2 | 3/1988 | European Pat. Off. |
| 0319309A3 | 6/1989 | European Pat. Off. |
| 0353592A2 | 2/1990 | European Pat. Off. |
| 0353592A3 | 2/1990 | European Pat. Off. |
| 0516274A2 | 12/1992 | European Pat. Off. |
| 0576291A2 | 12/1993 | European Pat. Off. |
| 0711995A2 | 5/1996 | European Pat. Off. |
| 0301699A2 | 2/1998 | European Pat. Off. |
| 0841557A2 | 5/1998 | European Pat. Off. |
| WO88/06062 | 8/1988 | WIPO |
| WO93/1818 | 9/1993 | WIPO |
| WO95/04263 | 2/1995 | WIPO |
| WO96/05488 | 2/1996 | WIPO |

*Primary Examiner*—Chris K. Moore

[57] ABSTRACT

A diagnostic microbiological testing system and method for microorganism identification (ID) and antimicrobial susceptibility determinations (AST). The system includes multiple-well test panels capable of performing ID and AST testing on the same test panel. Each test panel is inoculated with reagents, broth-suspended organisms, and placed into the instrument system. The instrument system includes a rotating carousel for incubation and indexing, multiple light sources each emitting different wavelength light, precision calorimetric and fluorometric detection, barcode test panel tracking and a control processor for making determinations based on measured test data. One light source includes a plurality of LEDs arranged in a linear array. Each of the LEDs' junction currents are controllable to produce a predetermined illumination profile.

35 Claims, 12 Drawing Sheets

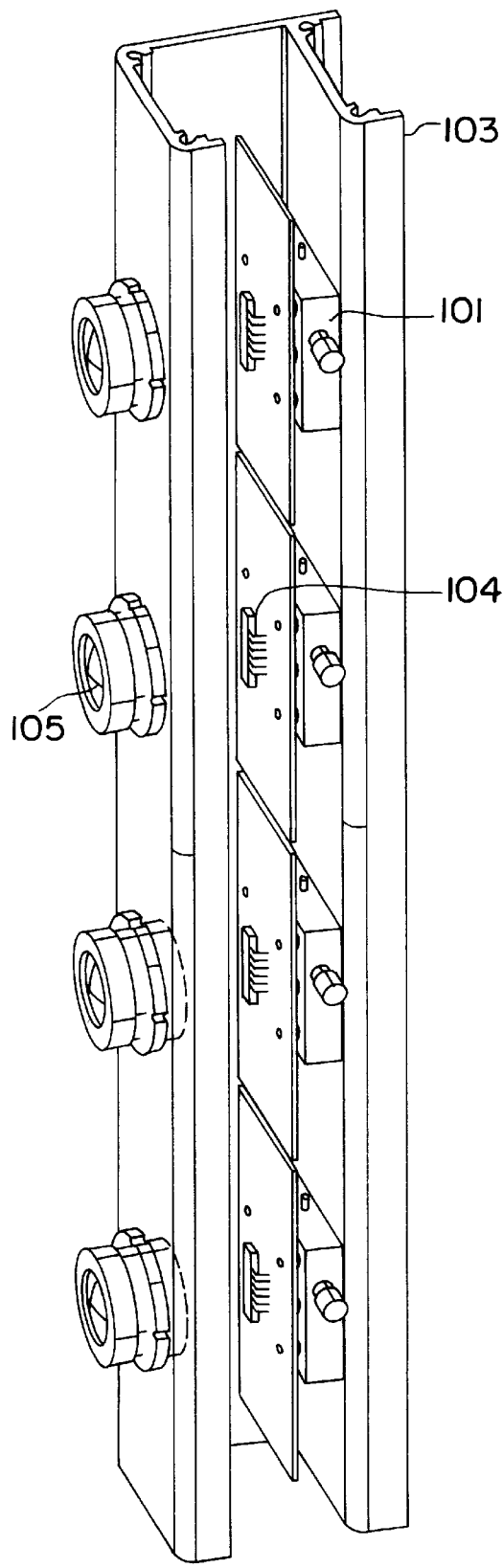
F I G. 7

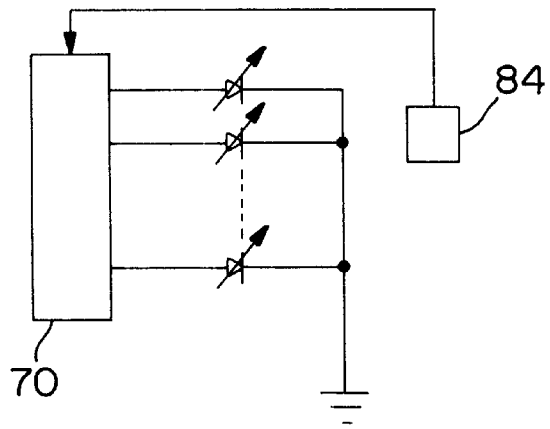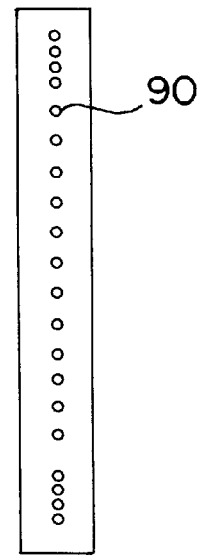
FIG. 13  FIG. 14
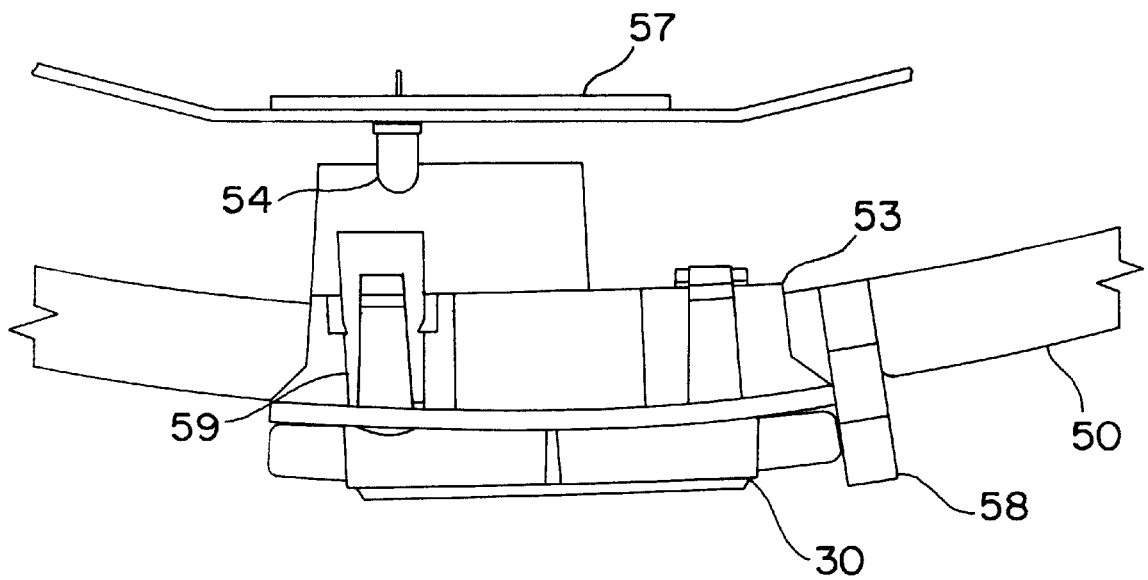
FIG. 15

AUTOMATED MICROBIOLOGICAL TESTING APPARATUS AND METHODS THEREFOR

CROSS-REFERENCE TO RELATED APPLICATIONS

This application claims the benefit of, and incorporates by reference the entirety of, U.S. Provisional Application No. 60/047,481, filed May 23, 1997.

BACKGROUND OF THE INVENTION

This invention relates to the field of microbiological testing.

Many conventional systems exist for performing tests on microbiological samples related to patient diagnosis and therapy. The microorganism samples may come from a variety of sources, including infected wounds, genital infections, cerebro-spinal fluids, blood and abscesses. From those microorganism samples an inoculum is prepared in accordance with established procedures which produce a bacterial or cellular suspension of a predetermined concentration. Further processing of the suspension may depend on the testing method employed.

These systems are used, for example, for identification of which microorganisms are present in a patient's sample. Typically, in such systems, reagents are placed into cupules, or test wells, of identification trays, which in the presence of an actively growing culture of microorganisms change color. Based on the color change, or lack thereof, the microorganism can be identified by the use of reference tables.

Other systems have been developed for susceptibility testing of microorganisms. These systems are used to determine the susceptibility of a microorganism in a sample to various therapeutics, such as antibiotics. Based on these test results, physicians can then, for example, prescribe an antimicrobial product which will be successful in killing or inhibiting the microorganism. In particular, qualitative susceptibility testing produces an indication of whether a microorganism is resistant or sensitive to a particular antibiotic, but does not provide an indication on the degree of sensitivity or resistance of the microorganism. On the other hand, quantitative susceptibility testing, provides an indication of the concentration of the antimicrobial agent needed to inhibit growth of the microorganism. The term minimum inhibitory concentration (MIC) is used to refer to the minimum concentration of the antimicrobial agent that is required to inhibit the growth of the microorganism.

The systems have certain drawbacks. For example, when performing identification and susceptibility testing, the test trays are incubated at a controlled temperature for an extended period of time. At predetermined time intervals, the wells of the test trays are individually examined for an indication of color change or other test criteria. This can be a long and tedious process if done manually by a technician. In addition, the incubation times for identification and susceptibility test trays may differ, or the optimal time to read a test result from the test tray may not be known in advance. Thus, a technician would need to read and record results for a specimen at several different times, sometimes long apart, which may cause assignment or correlation errors.

Automated systems are desirable in performing these tests to minimize the technician handling time, as well as to minimize the possibility of human error. In addition, automated systems that obtain results rapidly and accurately are preferred.

In this regard, a microbiological testing apparatus for the automatic incubation and reading of microbiological test trays is known. The test trays of this apparatus have a plurality of wells which contain the samples or agents to be tested. The trays are first placed in an incubator for a predetermined amount of time. The test trays are then moved to an inspection station. A light source is disposed above the tray and a pair of video cameras are disposed below the tray at the inspection station. Each video camera takes a video image of an entire tray. The video image signal of the entire tray is sent to an image processor to be analyzed.

The image processor requires uniform lighting over the inspection station. Consequently, the processor records the background light level of each pixel within an area of interest corresponding to each well of the tray to account for variability in the light source. The image processor processes the video image of the tray and determines the number of pixels, for a particular well, whose intensity exceeds a predetermined threshold for that area of interest. If the number of pixels exceeds a predetermined number, a positive result is assigned to that well. The image processor analyzes the binary partial results from the wells to determine the possible identity of the microorganisms. The binary partial results are compared to prerecorded patterns of results for each type of test tray to identify the sample in question.

A microbiological testing apparatus for detecting the presence of a fluorescence emitting reaction resulting from the interaction of a reacting agent and a sample for detection, susceptibility, and identification testing, is also known. In this apparatus, multiple trays having a plurality of test chambers are contained within a carousel. This carousel is rotated to move one of the trays close to a detection area. A positioning mechanism radially then moves that tray out of the carousel and into the detection area. A high-energy light source is disposed proximately to the thus positioned tray. The light source provides narrow-band light sufficient to produce an emission fluorescence from the reaction within test chambers, which in turn is detected by a video mechanism disposed opposite to the light source and behind the positioned tray. The video mechanism produces an image based on the emission wavelength.

Another test system is known for identifying bacteria using signals based on the intensity of monochromatic light reflected from specimens placed in a culture plate having a plurality of cells. A rotary disk containing six interference filters is interposed between a lamp and a group of optical fibers. The light from the lamp passes through a particular interference filter to produce monochromatic light of a certain wavelength. The filtered monochromatic light is guided by the optical fibers to be incident on respective cells of the culture plate. The disk is rotated so that the six different wavelength monochromatic lights are caused to be incident on the cells sequentially. The light reflected from the specimens is guided by additional optical fibers to corresponding phototransistors. A signal is derived for each specimen based on the intensity of the reflected monochromatic light. These signals are then analyzed to determine the identity of the specimen by calculating the difference, or ratio, between the signals and comparing that result with a reference value.

However, the above-described apparatuses fail to address all the requirements of a fully automated microbiological testing system. In particular, they are not capable of simultaneously performing both colorimetric- and fluorometric-type testing on multiple-well test panels that is needed to obtain more accurate test results. Further, these apparatuses are generally not designed to continuously gather test data from a plurality of multiple-well test panels in a quick and reliable manner. Moreover, the automated processing of these systems is limited.

SUMMARY OF THE INVENTION

The present invention provides a system that overcomes the above-described problems. In particular, the present invention provides an automated microbiological testing system that tests a plurality of multiple-well test panels, for identification and susceptibility, with a minimal amount of human intervention during the testing process. In addition, this system performs both colorimetric- and fluorometric-type testing. Moreover, this system quickly analyzes the gathered test data to produce accurate identification and/or susceptibility testing results.

In particular, one aspect of the present invention is directed to a diagnostic microbiological testing apparatus that has a carousel assembly on which is mounted a plurality of test panels. Each test panel has a plurality of wells, each of which is inoculated with a test inoculum fluid for producing a reaction. A plurality of light sources direct light of a predetermined range of wavelengths toward the wells of the test panels to cause the wells to emit or absorb light based on the reaction of the test inoculum fluid. A light detection unit, which may include a linear CCD, is disposed opposite to the light sources with at least one test panel being positioned between the light sources and the light detection unit. The light detection unit detects the light emitted from, or absorbed by, the wells of the test panels as the carousel assembly continuously rotates each of the test panels between the light sources and the light detection unit to permit light emitted from, or absorbed by, the wells of the test panels to be detected by the light detection unit. A controller receives a plurality of signals generated by the light detection unit, which correspond, respectively, to the light, which can be fluorescent or non-fluorescent, detected from each well. The controller then determines a test result for each well based on the received signals.

In another aspect of the present invention, an incubation chamber for a diagnostic microbiological testing apparatus is provided. This chamber includes a carousel assembly on which is mounted a plurality of test panels, each test panel having a plurality of wells for receiving a test inoculum fluid for producing a reaction. An enclosure surrounding the carousel assembly prevents intrusion of ambient light into the incubation chamber. The enclosure has a door for providing access to carousel assembly. A drive system continuously rotates the carousel assembly to directly position the test panels for testing by the diagnostic microbiological testing apparatus. A heating unit heats the incubation chamber and a temperature controller controls the heating unit to maintain the temperature within a predetermined temperature range.

In yet another aspect of the present invention, methods of operating, and computer mediums which include instructions for controlling, a diagnostic microbiological testing apparatus are provided. For example, one method includes the steps of (a) rotating a carousel of the testing apparatus to position a test panel mounted thereon between a light source and a light detection unit of the testing apparatus, (b) directing light from the light source toward the test panels, (c) detecting with the light detection unit the light transmitted or emitted from, or absorbed by, each of the wells of the test panels due to the test reaction, (d) generating with the light detection unit a signal corresponding to the light detected from each of the wells, and (e) determining a test result for each of the wells based on the generated signal.

In yet another aspect of the present invention, an apparatus is provided including a light source capable of producing a composite light signal having light elements of variable intensity, and a controller adapted to control the light source using an illumination profile. The apparatus may also include a light detection unit, and an optics system capable of directing the composite light signal toward the light detection unit. The illumination profile may be used to correct optical inefficiency in the optics system or changes in the illumination output of the light source.

In yet another aspect of the present invention, a light source including a plurality of LEDs arranged in a linear array is provided. The junction current of each LED is controllable to produce a predetermined illumination profile.

In yet another aspect of the present invention, a light source including a plurality of LEDs arranged in a linear array having two ends, each end having a group of LEDs of the plurality of LEDs. The group of LEDs is geometrically compressed to produce a greater intensity of light. The LEDs may include red, green and blue LEDs arranged in a predetermined order in the linear array.

In one further aspect of the present invention, an optics system is provided for a microbiological testing apparatus.

BRIEF DESCRIPTION OF THE DRAWINGS

These and other aspects, features and advantages of the present invention can best be understood by reference to the detailed description of the preferred embodiments set forth below taken with the drawings in which:

FIG. 7 is a schematic perspective view of the measurement system tower of the present invention.

FIG. 13 shows a circuit for controlling a light source module of the present invention.

FIG. 14 shows one embodiment of a light source module of the present invention.

FIG. 15 is a schematic perspective view of a portion of the panel carrier and test apparatus of the present invention.

DETAILED DESCRIPTION OF THE PREFERRED EMBODIMENTS

Figure 1:
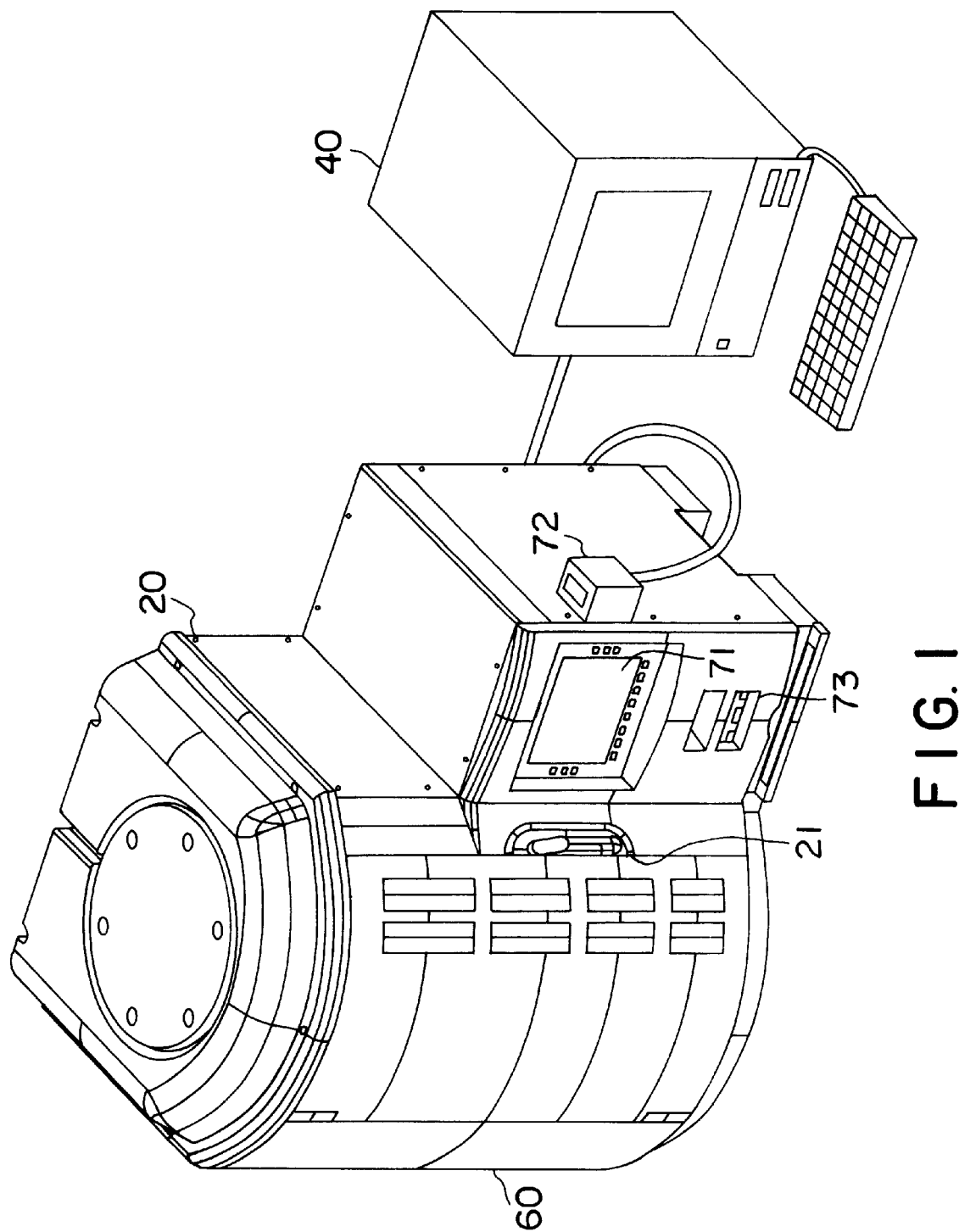
FIG. 1 is a front perspective view of the test apparatus of the present invention with the enclosure door closed.

The present invention provides a system and method for performing highly reliable microorganism identification (ID) and antimicrobial susceptibility determinations (AST). The present invention determines identification and susceptibility based on readings from wells 31 contained in ID/AST panels 30 (see FIGS. 3A and 3B). For example, in one embodiment, the wells 31 contain different reagent substrates and/or different antimicrobic dilutions which change optical character sometime after being inoculated with the organism. The detection method described below measures changes in absorption, scattering, and/or fluorescence. It may also measure luminescence. These changes are processed to determine the identification and susceptibility of the microorganism.

The present invention allows a technician, for example, after having inoculated the wells 31 of the ID/AST panel 30 with an unknown microorganism, to place that panel into an instrument 20 (shown in FIG. 1) where it is incubated at a set temperature, periodically interrogated for changes and analyzed for microorganism identification and antimicrobic susceptibility. The apparatus 20 holds a plurality of ID/AST panels 30 and provides positivity analysis results to the technician, as described below.

Figure 3A:
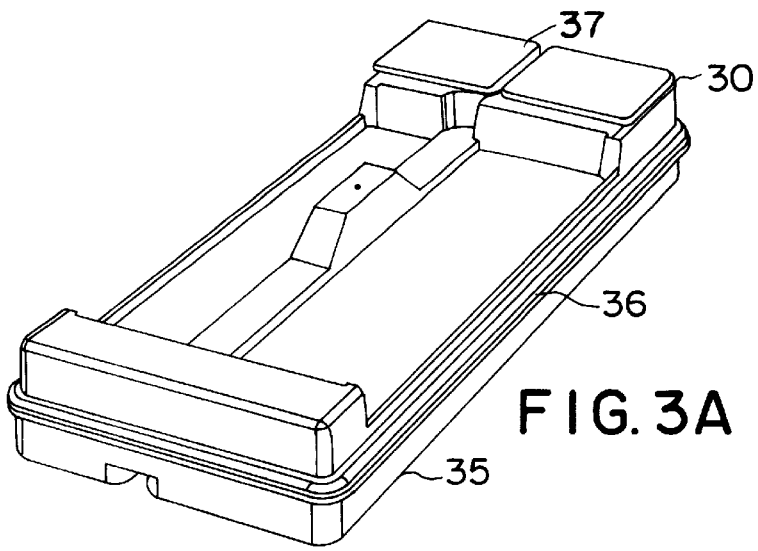
FIG. 3A is a perspective view of an ID/AST test panel of the present invention.
Figure 3B:
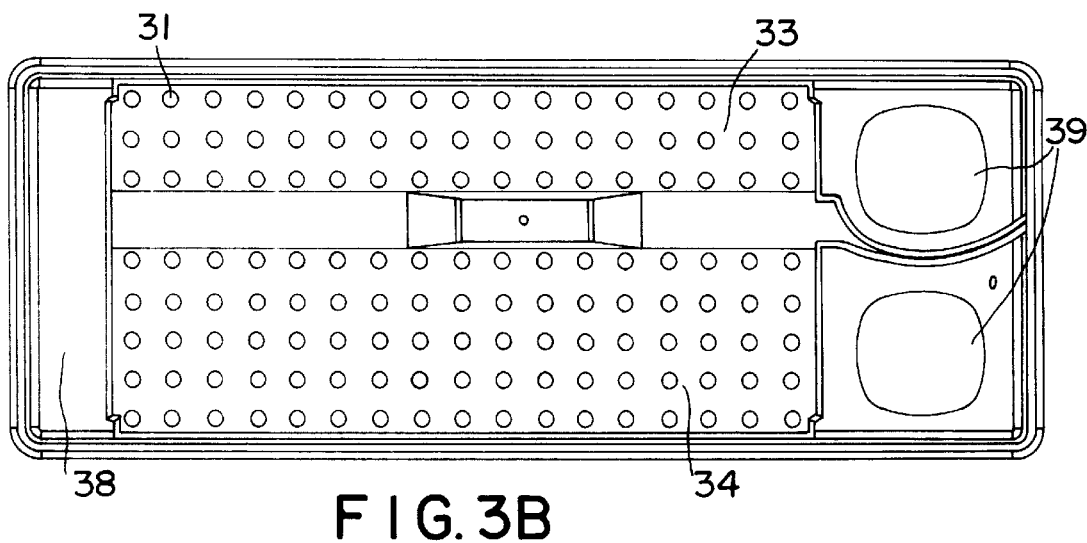
FIG. 3B is a top view of an ID/AST test panel of the present invention.
Figure 3C:
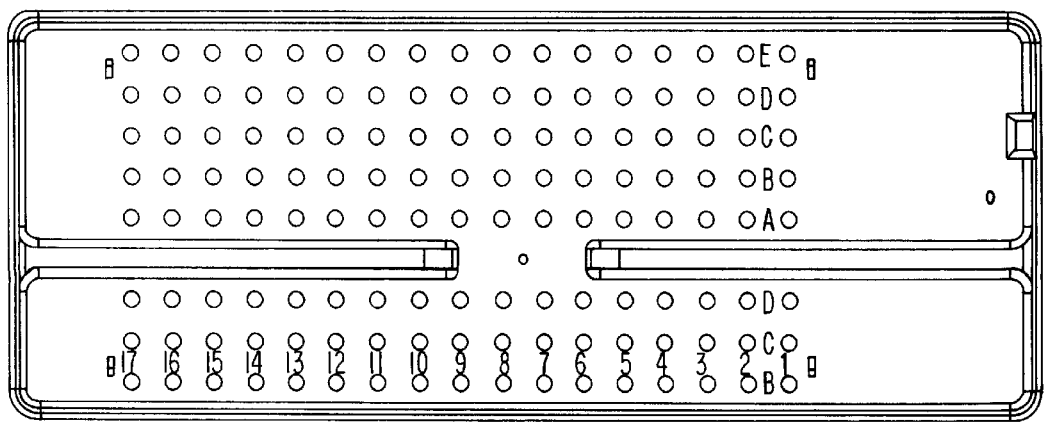
FIG. 3C is a bottom view of an ID/AST test panel of the present invention.

As shown in FIGS. 3A–3C, the ID/AST panels 30 are disposable devices which are inoculated with reagents needed for both ID and AST testing. The testing is performed on reactions generated by the samples and reagents placed in individual wells 31 on each ID/AST panel 30. The wells 31 are arranged on the ID/AST panels 30 as a two-dimensional array having rows and columns.

The instrument 20 is self-contained and sufficiently autonomous to test the ID/AST panels 30 and supply the appropriate test results. The instrument 20 stores, incubates and reads the ID/AST panels 30. The instrument 20 has a door 21 shown closed in FIG. 1 and open in FIG. 2 to allow for access to the interior of the instrument 20.

In one embodiment, as also shown in FIG. 1, a personal computer (PC) workstation 40 is communicatively connected to the instrument 20. The PC workstation complements the instrument's 20 microbiology information system reporting and data management features, which are discussed below. The PC workstation 40 provides tools to improve empiric therapy decision and identify therapy intervention instances. The PC workstation 40 also incorporates reporting tools to assist infection control and epidemiology.

Additionally, the PC Workstation 40 incorporates a relational database (not shown) on a hard drive. Finalized AST and ID test results are retained in the database for a minimum of 52 weeks. Statistically summarized data is retained for a greater time period. Patient and specimen information may be gathered through an electronic interface with the instrument 20 (not shown) or manually entered into the PC workstation 40.

Figure 2:
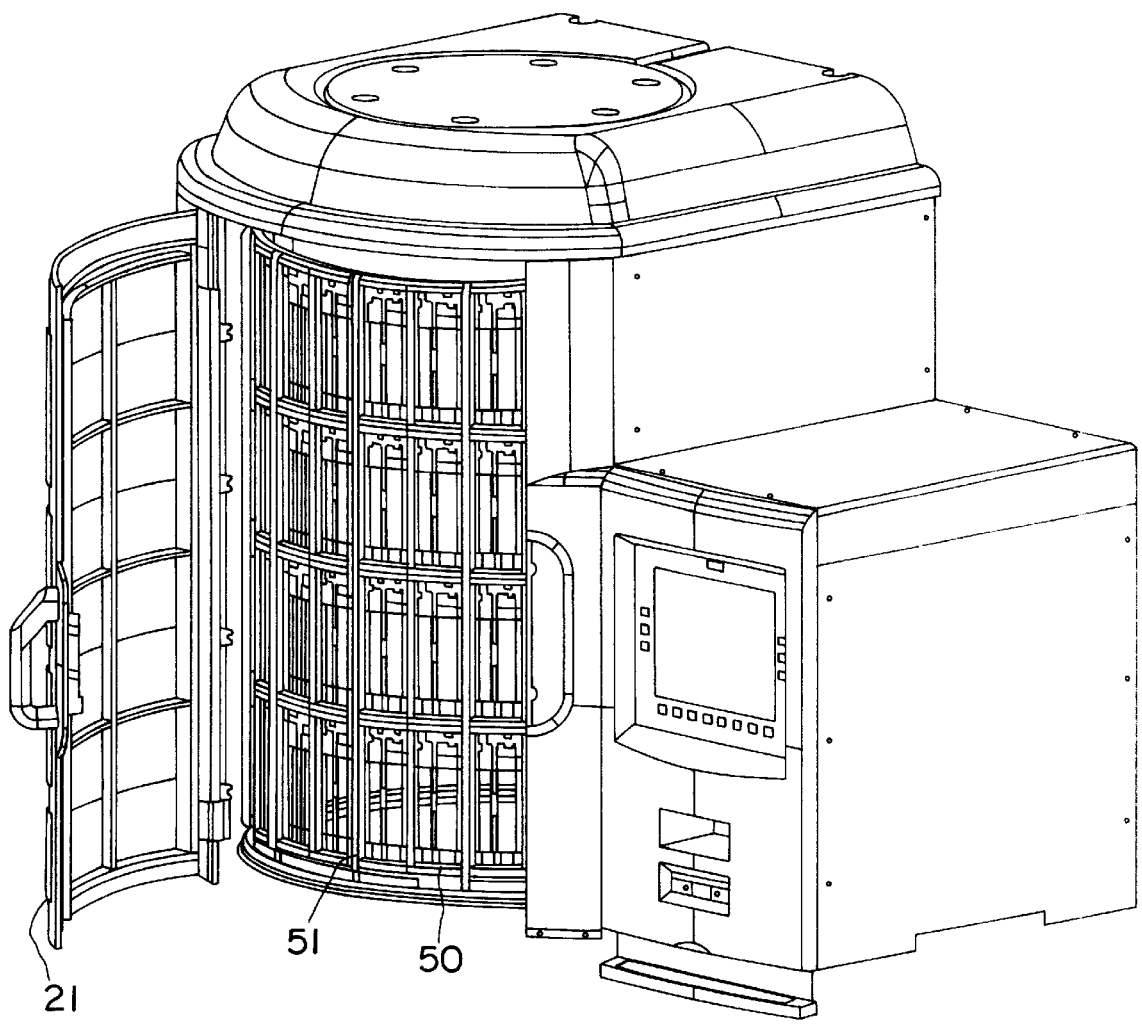
FIG. 2 is a front perspective view of the test apparatus of the present invention with the enclosure door open.
Figure 4:
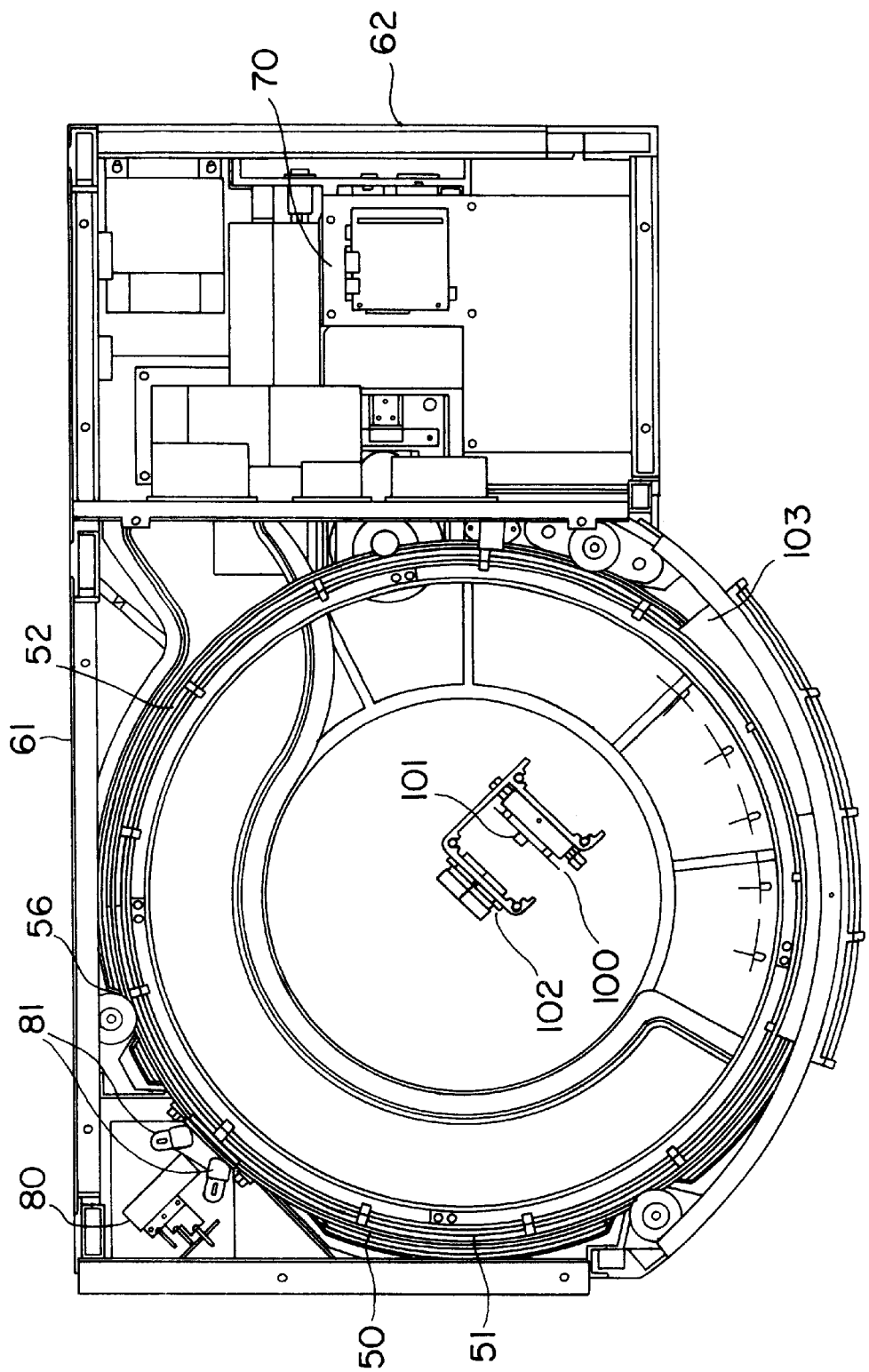
FIG. 4 is a schematic top view of the internal components of the apparatus of FIG. 1.
Figure 5:
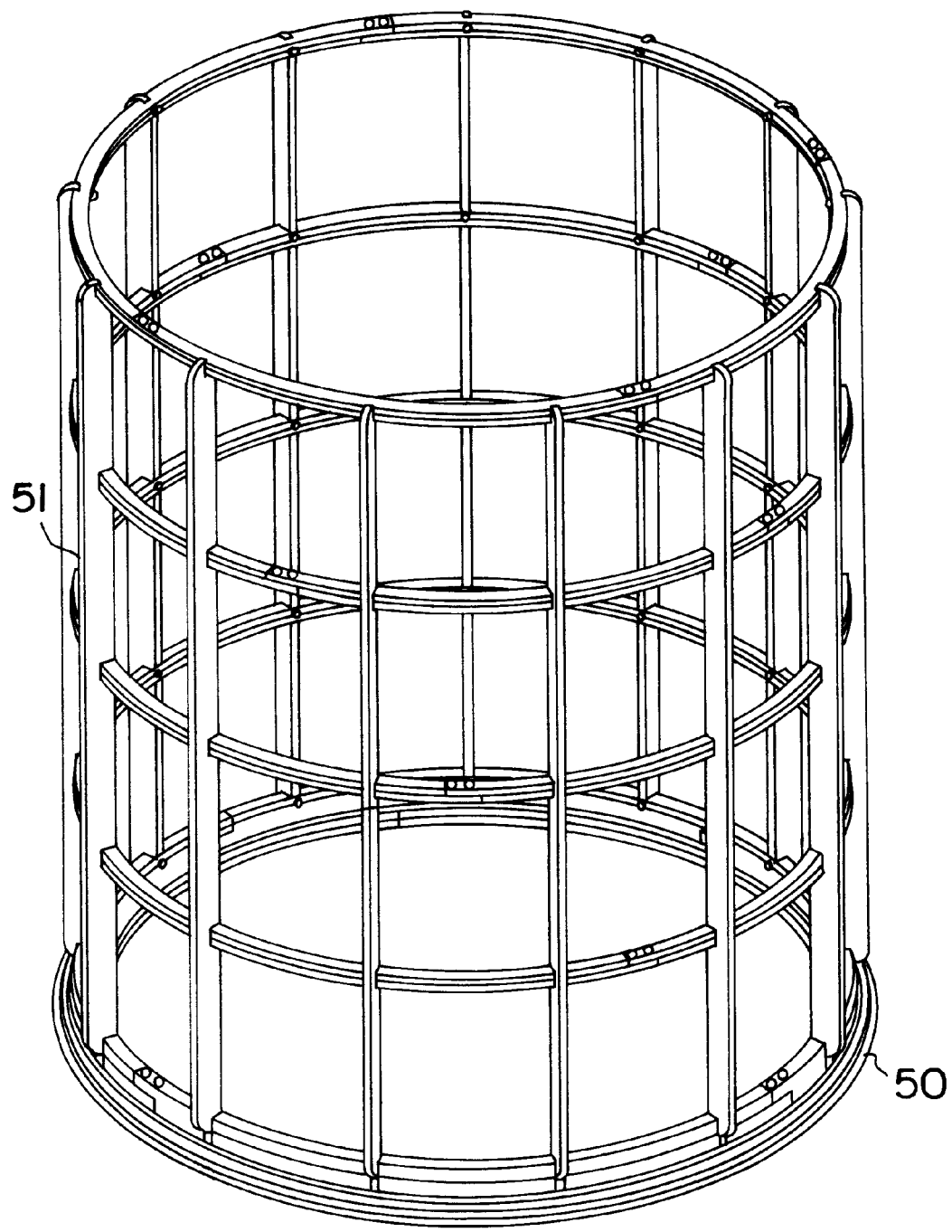
FIG. 5 is a schematic perspective view of the carousel assembly of the present invention.

The instrument 20 includes a carousel 50, as shown in FIG. 2. The carousel 50 includes an assembly 51 comprised of rings and ribs bolted to a drive ring 52 to form a cylindrical cage as shown in FIG. 5. The carousel 50 is mounted vertically in an instrument enclosure 60 (shown in FIG. 1). The instrument enclosure 60 defines the carousel compartment 61 and an electronics compartment 62 (shown in FIG. 4). The carousel compartment 61 is insulated to provide a substantially uniform temperature incubation environment, and is light-tight under normal operation to prevent ambient light from entering.

Figure 6:
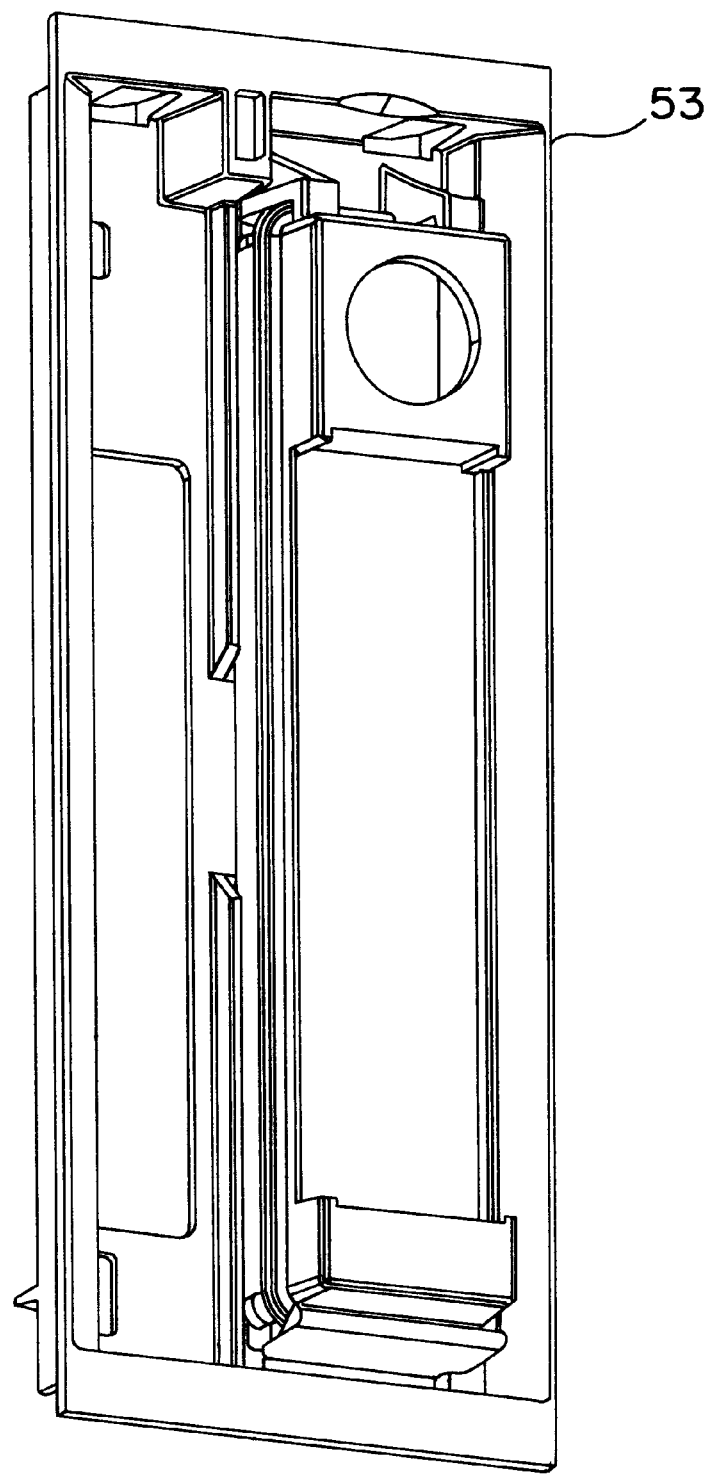
FIG. 6 is a perspective view of the panel carrier of the present invention.

Panel carriers 53 (shown in FIG. 6) are mounted in the assembly 51 which form four horizontal tiers with each tier having twenty-six panel positions. A total of one-hundred and four panel positions are provided. Of course, these numbers of tiers and panel positions are merely an example and may be changed to suit the requirements of any specified application as will be appreciated by one skilled in the art. The panel carriers 53 are used to mount the ID/AST panels 30 as well as other types of panels discussed below. The panel carriers 53 are designed such that improperly seated panels will not be retained by the panel carriers 53. When the ID/AST panels 30 are mounted in the four tiers of assembly 51, they are arranged to form substantially circular rows and vertical columns of wells 31. Within each tier, panel positions are numbered zero through twenty-five. Panel position zero is reserved for a normalization panel and is not accessible by an operator during normal operation of the instrument 20.

As shown in FIG. 15, indicator LEDs 54 are used to indicate which ID/AST panels 30 should be removed (i.e., when testing is complete), and which panel positions are available for new, untested ID/AST panels 30. The indicator LEDs 54 may be located in front of or behind each panel carrier 53. For example, as shown in FIG. 15, the indicator LED 54 is mounted in a printed circuit board 57 behind the panel carrier 53, which is positioned against a carousel rib 58. A light guide 59 may also be used to focus the light from the indicator LEDs 54 through a convex indicator surface.

The indicator LED 54 may be a three-color LED wherein different colors are used to indicate status/testing information. For example, red may indicate that a test is in progress; green may indicate that testing is complete; and yellow may indicate that a panel position is available for a new, untested ID/AST panel 30.

The carousel 50 also includes a drive system 56. The drive system 56 is mounted within the instrument enclosure 60 and exterior to the cylindrical cage formed by the assembly 51, as shown in FIG. 4. The drive system 56 drives the assembly 51, via the drive ring 52, at a predetermined and controllable angular velocity. One complete rotation of the carousel 50 is used to acquire and accumulate test data from only light frequency from each ID/AST panel 30 mounted within the assembly 51 (i.e., one data accumulation cycle).

A precision stepper motor is preferably used to provide accurate rotational control of the assembly 51. Of course, other types of motors can used which include servo-motors, synchronous motors and DC motors, for example.

An oil-treated felt pad is disposed against the drive ring 52 to ensure it remains properly lubricated. A poly-alpha-olefin oil, or similar oil, may be used to minimize oil spray and migration. In a preferred embodiment, a lubrication free bearing system can be used.

A home position flag magnet is affixed to the inner surface of the drive ring 52 corresponding to position zero of the assembly 51. As the assembly 51 rotates, a signal is generated by a Hall-effect sensor 55 mounted within the carousel 50 each time the home position flag magnet passes. This signal is used by the instrument 20 to keep track of the panel position as the assembly 51 is rotated. Of course, other types of sensors may be used for this purpose. For example, infrared and optical sensors may be used instead.

The temperature within the carousel compartment 61 is tightly controlled by means of an incubation heater, blower, and associated ductwork (none of which are shown) which distribute and recirculate the incubation air. The incubation heater includes one or more sensors 63 (shown in FIG. 11) to monitor the temperature within the carousel compartment 61.

The incubation heater includes two heating elements wired in a three lead arrangement (not shown). An auto-resetting thermal circuit breaker is provided in the third, common lead to protect against heater over-temperature conditions. Should the carousel compartment 61 temperature rise above a first predetermined set point, power to the heat is interrupted. Power is reapplied when the temperature falls below a second predetermined set-point. The power supplied to the heater is controlled by a control processor 70.

Preferably, the carousel compartment 61 is continuously maintained at a temperature of 35° C. with the first and second predetermined set points being set at 39° C. and 33° C., respectively. However, as will be appreciated by one skilled in the art, other temperature settings may be used to achieve the particular testing requirements.

In one embodiment, four barcode scanners (not shown) are mounted on a scanner tower (not shown) located within the carousel compartment 61, either within or exterior to the circumference of the assembly 51. One barcode scanner is provided for each tier of the assembly 51. The barcode scanners are capable of reading barcoded labels (not shown) affixed to each ID/AST panel 30 as the panels are rotated via the assembly 51. The barcode scanners are supported in proper relation to the ID/AST panels 30 mounted on the assembly 51 and are held at a proper scanning distance by the scanner tower.

The information read by the barcode scanners is used by the instrument 20 to correlate specific panel sequence numbers to test data gathered from the panels. Preferably, the barcode scanners are capable of reading Code-128 Numeric information. However, other known conventional barcode formats may be used instead to label the ID/AST panels 30. In another embodiment, a barcode reader (not shown) is installed behind the instrument front panel 71. The barcode reader is used to scan barcode labels affixed to either side of the ID/AST panels 30 before the ID/AST panels 30 are mounted in the carousel compartment 61. This allows, for example, the operator to affix supplemental barcoded information on each ID/AST panel 30. The supplemental barcoded information could be, for example, a hospital-applied accession label. In this embodiment, the barcoded labels can be scanned, and the particular ID/AST panel 30 can then turned over to scan the supplemental barcoded information, this then links the ID/AST panel 30 to the supplemental barcoded information. Conventional barcode formats are supported by the barcode reader.

In another embodiment, a hand-held scanning barcode wand 72, as shown in FIG. 1, is operatively connected to the instrument 20. The barcode wand 72 may be used in the same manner as the barcode reader (e.g., to scan operator generated accession linkage, or to scan barcodes too large to be affixed to the ID/AST panels 30). Conventional barcode formats are supported by the barcode wand 72.

A panel position sensor for each tier is also mounted on the scanner tower. Panel position flags, integrated with the panel carriers 53, are read by the panel position sensors. Upon scanning the leading edge of the panel flag position flags, the panel position sensors generate a signal used to provide test data acquisition timing for each ID/AST panel 30.

As shown in FIG. 4, a plurality of light source assemblies are mounted within the carousel compartment 61 and exterior to the circumference of the assembly 51. In a preferred embodiment of the present invention, the light source assemblies comprise a visible light source assembly 80 and an Ultra-Violet (UV) light source assembly 81 (shown in FIG. 11).

The visible light source assembly 80 includes four visible light source modules and a supporting tower. The supporting tower aligns one visible light source modules with each tier of the assembly 51. At any given time, one column of wells from the ID/AST panels 30 can be illuminated by the visible light source modules.

In one embodiment, each visible light source module includes three parallel vertical columns of sixteen light-emitting diodes (LEDs) each. The first column consists of red LEDs, the second green LEDs and the third blue LEDs. A holographic diffuser plate 82 is located in close proximity to the ID/AST panels 30 mounted in the assembly 51. The holographic diffuser plate 82 diffuse the illumination energy from each column of LEDs (when energized). Each column of LEDs is mounted in the visible light source modules to maintain a fixed distance from the diffuser plate 82. Cylindrical lenses may be used to focus the illumination energy from each column of LEDs onto the vertical well columns of the ID/AST panels 30. The illumination axis for each column of LEDs is made coincident for the red, green and blue illumination. Thus, each well column sees a uniform stripe of either red, green or blue illumination, depending upon which column of LEDs is energized.

Each visible light source module may also be fitted with a partially reflecting beamsplitter. The beamsplitter would cause a portion of the illumination energy from the LEDs to be incident on a source monitor photodiode 84. The signal from the source monitor photodiode 84 is then used to correct the light intensity of each of the LED columns as necessary. For example, the signal from the source monitor photodiode 84 may be used to compensate for fluctuations in illumination output during LED warm-up at start time, via an illumination profile discussed below. This allows the instrument 20 to begin testing more quickly because the testing would not have to wait for the LEDs to warm-up (i.e., to reach a steady-state illumination output).

The visible light source modules are spaced vertically and positioned properly with respect to the ID/AST panels 30 mounted in each tier of the assembly 51 by the supporting tower. The supporting tower can also include mounts for the beamsplitters, the holographic diffuser plates 82 and the cylindrical lenses.

Figures 9, 10A, 10B:
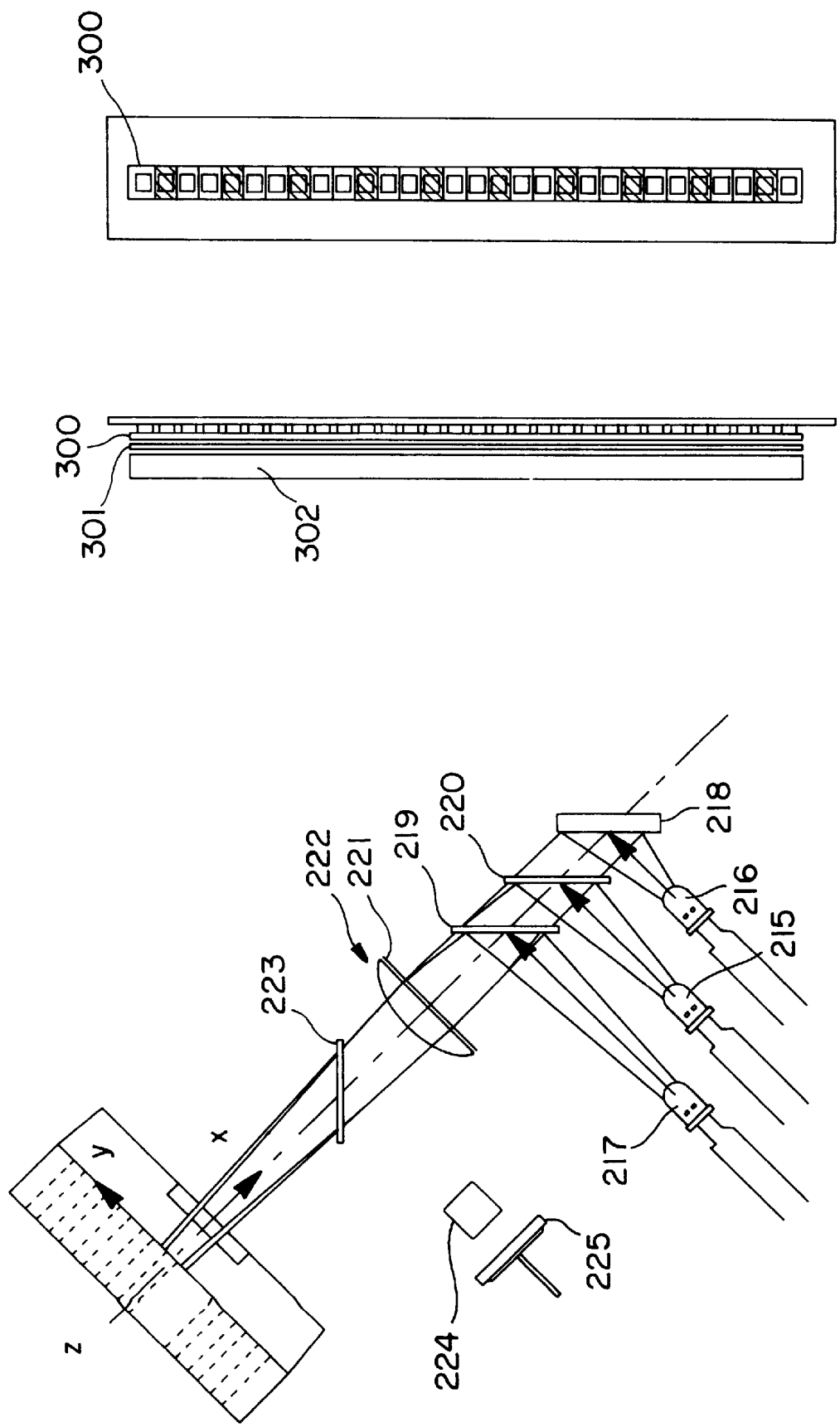
FIG. 9 shows one embodiment in which solid-state LEDs and dichroic color separation filters are used.
FIGS. 10A and 10B are respectively front and side views of another embodiment in which surface mount LEDs and color separation filters are used.

In another embodiment, shown in FIG. 9. Other arrangements are possible for the visible light source used in the present invention. FIG. 9 shows an overhead view of a tri-spectrum arrangement (e.g., red, green and blue) using three LEDs (215, 216, 217). A bank of more or less than three LEDs can be used at any single Z-axis location. Groups of the LED banks can be stacked as deep as needed in the Z-axis direction so as to cover the entire length of the ID/AST panels 30.

Light from the LED 216 is reflected 90° by a first surface mirror 218 along the illumination axis. Some of this light passes through the dichroic filters 220 and 219, diverging to a holographic diffuser 221 in the X direction. Some of the light is rejected by each filter and continues through in the Y direction. The holographic diffuser 221 acts to homogenize the light in a defined manner. The filtered, homogenized light passes through a cylindrical lens 222 which concentrates it into a homogenous light stripe of a prescribed width at the ID/AST panel 30.

A portion of the light focused at the ID/AST panel 30 is redirected 90° by a planar glass optical flat 223 into a light pipe 224 that concentrates it to a source monitor 225. A signal generated by the source monitor 225 is used to correct the light intensity from each of the groups of the LED banks as necessary.

Similarly, some of the light from the LED 217 is reflected 90° by the dichroic filter 219 and this filtered energy is optically processed in the manner described above. Again, some light from the LED 215 is reflected 90° by dichroic filter 220 and this filtered energy is optically processed by the remaining components in the optical train as described above.

In another embodiment, a solid-state visible light source assembly is shown in FIG. 10A. A plurality of surface mount LEDs 300 (SMLEDs) are placed in an array which coincides with a column of wells 31 of the ID/AST panels 30. The SMLEDs are arranged in a repeated pattern in the array. For example, the first SMLED can be red, the second a green SMLED and the third a blue SMLED. This pattern is then repeated the length of the array. As many banks of SMLEDs as needed can be arranged to properly illuminate the area desired.

In this embodiment, the illumination axis of the array of SMLEDs is arranged in the same line with the wells 31. Consequently, the SMLEDs 300 are energized based on their respective spectral content (i.e., red, green or blue illumination). As before, this light is further conditioned to homogenize and concentrate it onto the target using a holographic diffuser 301 and a focusing lens 302, as shown in FIG. 10B. As described above, a beamsplitter and source monitor are also used in this embodiment.

Because the illumination intensity tends to fall off at the ends, each column of LEDs, the holographic diffuser plate 82, and cylindrical lenses can be made physically longer than the active area of the ID/AST panels 30. In order to compensate for the light fall-off at the ID/AST panel 30 extremes caused by the optical inefficiencies, the intensity of illumination near the ends of each LED column is boosted to improve uniformity. One way this may be accomplished is by driving the LEDs near the ends of each column with higher currents, which increases the intensity of the light at those ends.

Figure 12A:
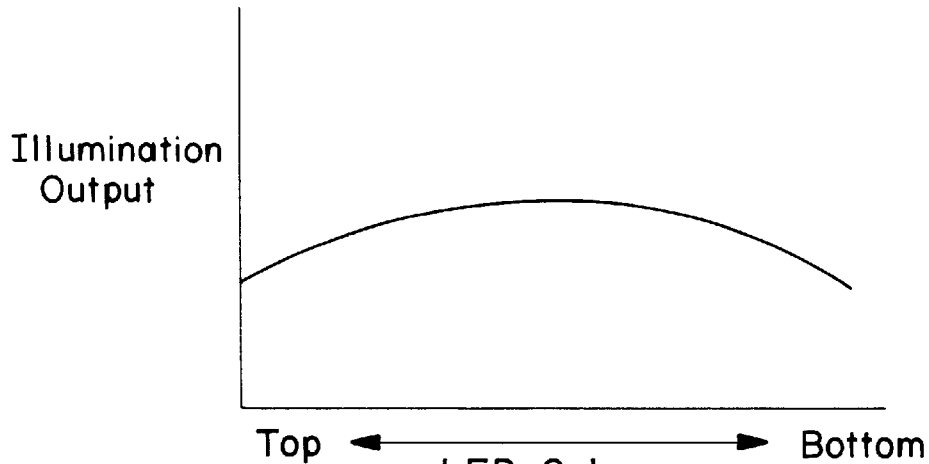
FIG. 12A shows a graph of an illumination output from a light source module.
Figure 12B:
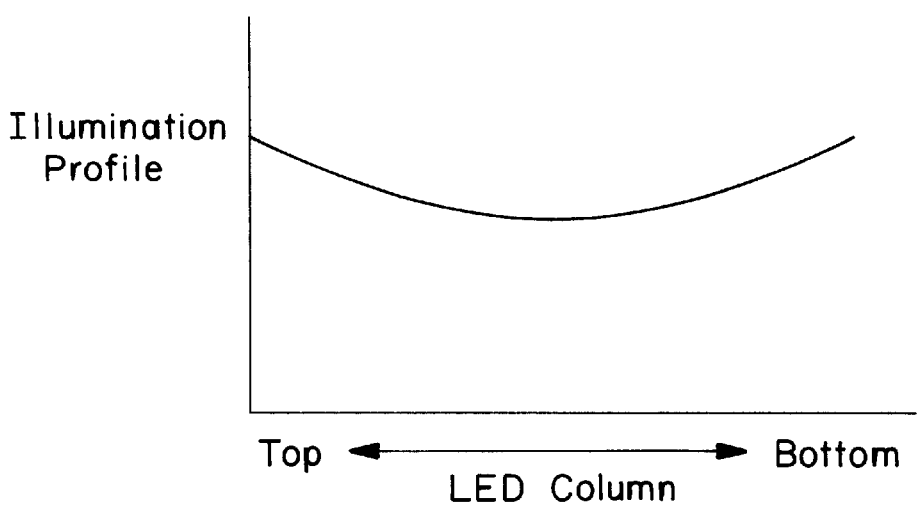
FIG. 12B shows graph of a illumination profile used to drive the light source module of the present invention.
Figure 12C:
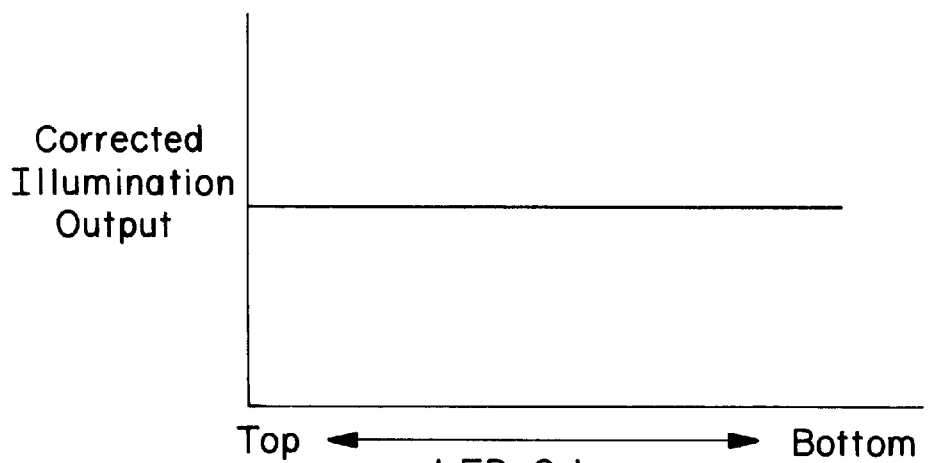
FIG. 12C shows a graph of an illumination output from the light source module of the present invention resulting from the illumination profile of FIG. 12B.

The junction current used to drive the LED or SMLEDs, discussed above, can be controlled using a computer program stored in the control processor 70, as shown in FIG. 13. Illumination profiles can be used to dynamically drive the LEDs to compensate for optical inefficiency. As shown in FIG. 12A, when the LEDs of one column are all driven with the same drive current, the illumination output from the LEDs at the ends (i.e., top and bottom) of the columns, as measured by an optical detection system 100, is less than the illumination output from the LEDs near the center of the column. FIG. 12B shows an illumination profile in which the LEDs at the ends of the column are driven with a higher current. This produces a greater illumination output from the LEDs at the ends of the column as compared to the LEDs near the center of the column. FIG. 12C shows the resulting illumination output, as measured by the optical detection system 100, of the LED column when driven by the illumination profile of FIG. 12B.

While the illumination profile of FIG. 12B shows a complementary profile used to produce a uniform illumination output, a variety of illumination profiles can be used. These profiles may be selected based different criteria, such as, the type of test panel used, the type of test to be performed, or feedback signals. For example, a proportional feedback control loop using signals from the source monitor photodiode 84 can correct for light intensity changes during testing, during LED warm-up, or for long term degradation of the LED junction current. Other types of feedback correction systems may be based on temperature changes within the instrument 20 or on signals from a normalizer panel, discussed below.

Another way of compensating for the intensity fall-off at the ends of the column is to geometrically compress the spacing of LEDs or SMLEDs at the ends of each column, i.e., a stacked LED configuration at the ends. As shown in FIG. 15, LEDs 90 at the ends of the linear array are geometrically compressed. This type of configuration compensates for degradation of optical efficiency at the ends of the columns. When the LEDs are placed closer together, the intensity of the illumination increases. Preferably, the LEDs should be compressed to produce an intensity inverse to the fall-off. For example, an optical coupling roll-off of 90% at the column ends (relative to the column center) may be compensated by decreasing the LED center-to-center distance at the column ends by a factor of ten.

Returning to FIG. 11, the UV Light Source assembly 81 includes two tubular UV cold-cathode lamps. Hot-cathode lamps may also be used. Suitable lamps may be obtained from Voltarc (VTI, Waterbury, Conn. 06705). The radiation passes through excitation filters 85. The excitation filters 85 eliminate unwanted spectral components present in the output of the lamps.

Figure 11:
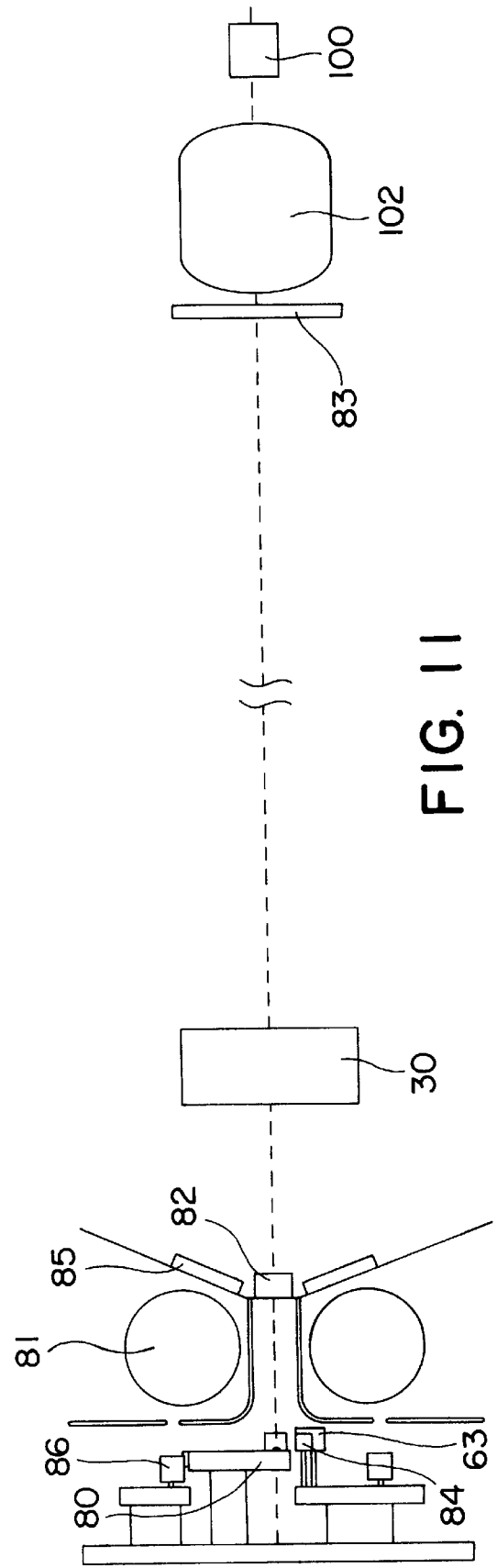
FIG. 11 is a schematic view of the configuration of the light source assemblies of the present invention.

As shown in FIG. 11, the lamps are disposed on either side of the primary illumination axis so that one column of vertically-aligned ID/AST panels 30 are illuminated simultaneously. There is no need to align the UV light sources along the primary illumination axis. Adjustment of the illumination intensity is performed by altering the high-frequency power applied to the lamp and its series inductance. This is controlled by the control processor 70. Only one lamp is illuminated at a time. The other lamp is held in reserve.

In this embodiment, the fluorescence reaction is stimulated via a direct transmission mode of the light through the wells 31. However, a reflective mode may also be used which would require repositioning of the UV light sources.

A UV source monitor photodiode 86 for each lamp is positioned to intercept a small portion of the radiation leaving the lamp. The resulting signal is used to monitor the lamp's intensity. This signal also allows the control processor 70 to detect a decrease in the lamp's intensity so that the other reserve lamp can be activated if necessary.

The active lamp is operated at full power only when UV excitation measurements are being taken. Otherwise, the lamp is dimmed to low power to conserve lamp life, or turned off, to prevent optical interference with readings using the visible excitation light sources discussed above. In addition, an emission filter 83 (shown in FIG. 11) is used eliminate any unwanted spectral components that may be introduced by the lamps. For example, the emission filter 83 filters out the UV light wavelengths of the lamp. The lamp current is raised to operating level for test data acquisition by means of a signal line controlled by the control processor 70 (i.e., switching the lamp from low- to high-intensity operation).

A UV source power supply 92 powers the active lamp. As discussed above, adjustment of the lamp's intensity is accomplished by varying the frequency of high voltage excitation applied to the lamp and its series inductance. An increase in frequency causes a decrease in lamp current as the inductive reactance increases, which in turn causes a decrease in lamp intensity.

The UV source power supply 92 also includes high voltage reed relays (not shown) to transfer power from the active lamp to the reserve lamp as directed by the control processor 70. As discussed above, lamp transfer occurs when the source monitor photodiode detects a significant decrease in the intensity of the active lamp.

In operation, the visible light source assembly 80 and the UV light source assembly 81 are sequentially energized. After one complete rotation of the carousel 50 (i.e., one data accumulation cycle), another type of wavelength illumination is energized. For example, in one arrangement, each column of LEDs (i.e., red, green and blue) contained in the visible light source modules are energized sequentially, then the UV light source module is switched to full power, each light source being active for one complete of carousel 50 rotation. This enables the instrument 20 to gather test data from each ID/AST panel 30 based on different types of wavelength light. In a preferred embodiment, the sequence is UV warm up, UV reading, followed by red, green and blue readings.

As shown in FIG. 4, the optical measurement system 100 is disposed approximately within the center of the assembly 51 such that it is aligned to the visible light transmitted through each well 31 of the ID/AST panels 30 during excitation with red, green or blue illumination from the visible light source modules. Visible fluorescent radiation is similarly detected from the wells 31 excited by the UV light. As discussed above, the emission filter 83 eliminates unwanted spectral components that may be present in the output signal before detection by the optical measurement system 100. In another embodiment, near-Infrared (IR) light can be used to perform the optical test scans.

As will be appreciated by one skilled in the art, a variety of means may be used to measure changes in optical characteristics. For example, photodiodes or an array of photosensors may be used.

Figure 8:
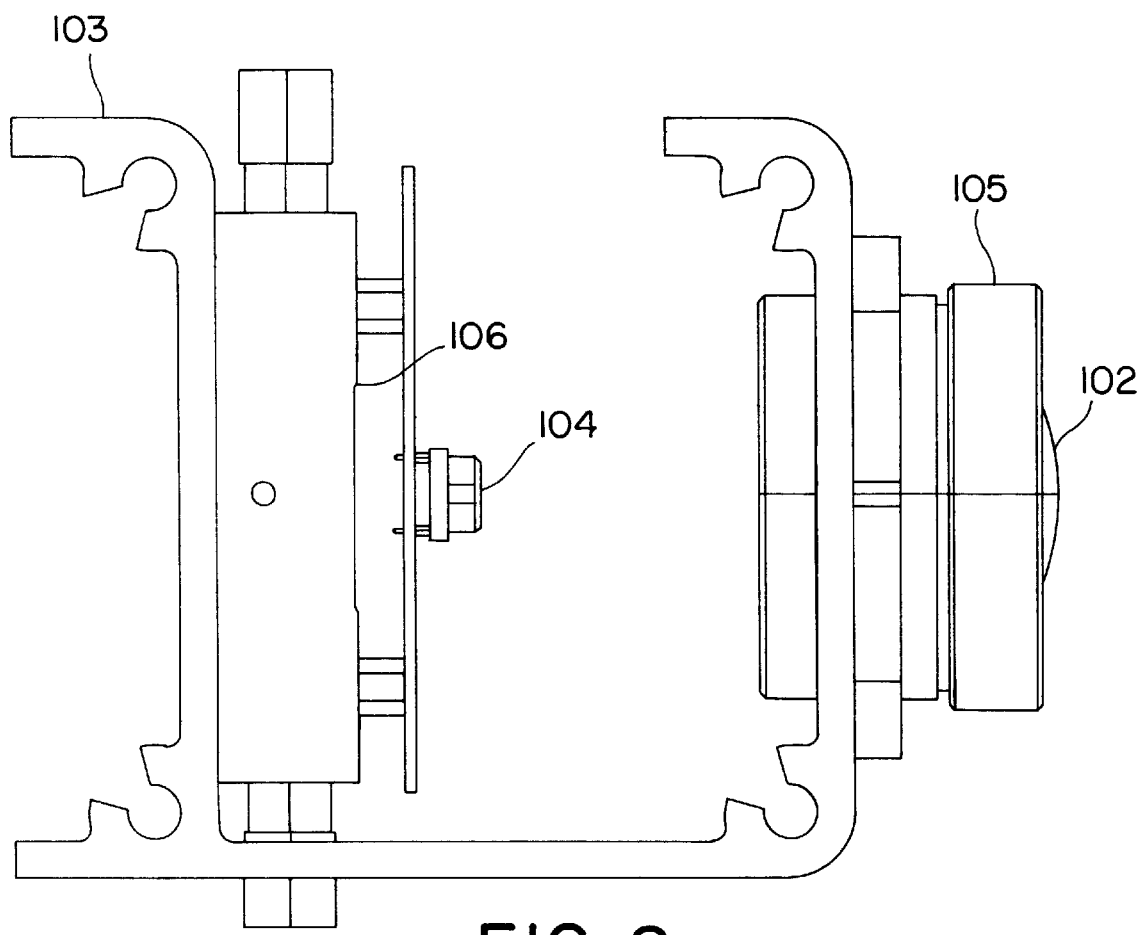
FIG. 8 is a schematic perspective view of the CCD detection module of the present invention.

In a preferred embodiment, a plurality of CCD detector modules 101 and lens assemblies 105 (shown in FIGS. 7 and 8) are provided, one for each assembly 51 tier. The CCD detector modules 101 and lens assemblies 105 are supported on a measurement system tower 103. The measurement tower 103 supports the lens assemblies 105 and the CCD detector modules 101 so that they are oriented in alignment with the optical axis of one well column of the ID/AST panels 30.

The lens assemblies 105 include objective lens 102. The light from of each panel well column is focused onto the CCD arrays 104 by the objective lens 102.

Each CCD detector module 101 includes a CCD array 104. A 2048-pixel linear CCD array, for example, may be used. The CCD arrays 104 detect and measure the intensity of light transmitted through each well 31 when illuminated by the red, green and blue LEDs. Visible fluorescent light is similarly detected by the CCD array 104 under UV light excitation. Alternatively, the UV light excitation can be positioned such that the CCD arrays 104 detect the reflected, or absorbed, visible fluorescent light from the wells 31.

The CCD arrays 104 are positioned relative to each tier to provide ample illumination over-scan of all the locations of the wells 31 in any column of the ID/AST panels 30. The only light detectable by the CCD arrays 104 is the monochromatic light passing through, or the visible fluorescence emissions from the wells 31. Thus, the CCD arrays 104 detect and measure the light intensity of the wells but not of any other object illuminated by the light source assemblies. Y-axis column information, which represents one vertical slice of information, is scanned electronically by the CCD arrays 104. Multiple slices of information are required to detect and measure the light intensity from one column of wells. X-axis information is accumulated with the rotation of the assembly 51 (i.e., the ID/AST panels 30 are rotated so that the next vertical slice of information can be scanned).

Sensitivity of the CCD detection modules 101 is governed by the integration time selected for each CCD array 104. As understood by one skilled in the art, light is composed of individual photons. Each photon has an extremely small amount of energy associated therewith. The amount of time necessary to charge the pixels is called the integration time. Varying amounts of photons emitted from, or absorbed by, the individual wells 31 are incident on individual pixels within each CCD array 104 and charge the pixels to different levels proportional to the incident light.

The integration time for the CCD arrays 104 in the present invention is variable. This gives the present invention the flexibility of having ID/AST panels 30 that contain substrates with a variety of optical properties (i.e., transparent or optically dense). From information gathered from the barcode label, the integration time is set to control the gain for each ID/AST panel 30. The integration time for the next ID/AST panel 30 is set before it is illuminated by the light sources. In one embodiment, a default integration time is selected to be approximately 4.0 milliseconds. Other integration times may be selected by the control processor 70 as needed during testing of the ID/AST panels 30.

Data processing of the accumulated pixel information is accomplished by four detector microcontrollers (and supporting circuitry) 106, one for each CCD detector module 101. Each detector microcontroller 106 receives and processes data from the associated CCD arrays 104. This data is collected from each well 31 when illuminated by the red, green and blue LEDs and excited by the UV light during the rotation of the ID/AST panel 30 via the assembly 51.

In operation, the detector microcontrollers 106 use the panel flag signal generated by the panel position sensors to initiate panel data acquisition via the CCD arrays 104. As mentioned above, the panel flag signal is generated as the panel position flags pass the panel position sensors during rotation of the assembly 51. This signal is used as a timing start point for test data gathering.

The carousel 50 rotates continuously while the detector microcontrollers 106 receive test data gathered by the CCD arrays 104. In a this embodiment, the CCD arrays 104 measure more than one variable in parallel (absorption, turbidity and/or fluorescence) from essentially the same spatial location. The measurements are taken by the CCD linear arrays as the ID/AST panels 30 "fly by." All the detector microcontrollers 106 simultaneously receive the test data from the CCD arrays 104 as a well column of the ID/AST panels 30 is illuminated by the light from the visible light source assembly 80, or excited by the UV light source assembly 81.

A registration mark (not shown) on each of the ID/AST panels 30 is located by performing an algorithmic search on the series of linear array data scans. Knowing how many steps the step motor of the drive system 56 have occurred between the timing start point and the registration mark, in addition to the first CCD array 104 pixel where the registration mark starts, gives the information needed to locate precisely any well 31 on the scanned ID/AST panel 30.

There are two light source normalization processes that occur during the test data acquisition process. The first reduces the effects of spatial inhomogeneities from well to well. The second normalization process involves monitoring the instantaneous source intensity simultaneous with the CCD array 104 test data acquisition.

A normalizer panel serves as a reference panel for instrumental correction of the optical measurement system 100. Each tier of the assembly 51 contains one normalizer panel which resides in position location zero on each tier. The normalizer panel contains a matrix of absorbers in ID/AST panel-well format. The normalizer panel is constructed such that it has a nominal geometry equivalent to the ID/AST panels 30. The readings from the normalizer panel do not change over time and transmits the same light intensity when illuminated uniformly. By measuring each normalizer panel well's output, a correction factor for each well is created to eliminate any nonuniformities in well to well source intensity, to correct individual well signals for losses occurring in the optical system, and to compensate for the reduction in LED output over time. Test data collected from each ID/AST panel 30 in a tier of the assembly 51 is corrected (normalized) for any changes in the optical system since the normalizer panel for that tier was last read.

In one embodiment, a selectably energized monochromatic light source provides linear illumination for a column of uniform wells of the normalizer panel. The profile of illumination intensity along the column is piecewise adjusted to provide uniform detector response for all the wells in the column of the normalizer panel. The columns of all the ID/AST panels 30 are then illuminated with this profile. The normalizer optical response of each well in the ID/AST panel 30 is thereby measured with uniform sensitivity for all the well locations within each column.

As mentioned above, the signal from the source monitor photodiode 84 is used to determine any changes in visible light source assembly's 81 light intensity as the carousel assembly 51 rotates. While the normalizer panel is used to monitor relative spatial variations of intensity, the source monitor photodiode 84 enables the present invention to monitor quasi-absolute intensity as it fluctuates throughout a single rotation of the carousel assembly 51 or varies over a long period of time. The source monitor photodiode 84 is monitored simultaneously with each CCD array acquisition. The detector microcontroller 106 has two correction factors to apply to each set of test data gathered so that any differences between test data scans are due only to the optical properties of the reagents in the wells 31.

Each detector microcontroller 106 also receives data from a CCD dark current scan. Dark current correction is applied to the data on a per-pixel basis.

In an alternative embodiment, a fluorescent visible light source and a filter wheel (not shown) can be used instead of the visible light sources discussed above. The filter wheel contains a plurality of spectral filters. In this embodiment, for example, absorption and turbidity measurements are acquired in three consecutive rotations of the assembly 51, while fluorescence measurements are acquired during a fourth rotation. Upon completing the first rotation for normalization and registration mark locations (this is done for each of the panels per tier), the filter wheel indexes to it's first spectral filter. Upon reaching the normalizer panel, the filter wheel indexes the second spectral filter. Test data acquisition, normalization and the computation process, as described above, are repeated for each spectral filter within the filter wheel. After calorimetric measurements are performed, the visible fluorescent source is turned off. The filter wheel indexes an emission filter and fluorescence measurements are taken in a similar manner.

In order to reduce the post-processing burden, all pixel information not associated with ID/AST panel wells are eliminated. For example, the analog signal from the CCD array 104 can be digitized and the detector microcontroller 106 can then process the digitized signal accordingly. The test data for each well 31 (i.e., the light intensity information) is then averaged. The averaging is performed based on a perpixel value received from the CCD array 104 for each well 31. The averaging produces a single integer numerical value for each well 31. One numerical value is produced for each data accumulation cycle (i.e., red, green and blue illumination and UV light excitation). This information is then sent via a multi-drop serial data transmission protocol to the control processor 70.

In one embodiment, spatially averaging of an analog signal from the CCD arrays 104 is performed by the detection microcontroller 106 so as to eliminate unwanted optical and electrical artifacts from sample column data. The spatial averaging is performed using partial analog decommutation of the pixel intensity of the analog signal.

As shown in FIG. 4, the control processor 70 is mounted in the electronic compartment 62 of the instrument enclosure 60. The control processor 70 includes the instrument front panel 71, a keyboard 72, a computer readable medium drive 73 (e.g., floppy disk or CD-ROM drive), and a loudspeaker/audible alarm. The control processor 70 also includes an I/O interface board, a CPU, memory, an Ethernet interface circuitry, display driver circuitry (none of which are shown). The control processor 70 can also be provided with a mouse.

In operation, the control processor 70 performs the following functions by executing instructions stored in a computer readable medium. The control processor 70 senses the home flag magnet on the drive ring 52 via the hall-effect sensor 55. This is done in order to properly index the ID/AST panels 30 which are mounted on the assembly 51 while being rotated. High-level commands are sent to the detector microcontrollers 106 to initiate or stop testing of the ID/AST panels 30. The intensity of the UV light source assembly 81 is controlled based on the signal from the UV source monitor photodiode 86. The control processor 70 illuminates the status indicator LEDs 54 on the panel carriers 53. The indicator LEDs 54, as discussed above, identify which ID/AST panels 30 have been tested and can be removed from the assembly 51. The incubation temperature is also controlled by the control processor 70 via signal/control lines operatively connected to the incubation heater.

The control processor 70 also receives the data generated from the barcode scanners, the barcode reader and the barcode wand 72. As discussed above, the data from the barcode scanners is used to correlate the test data gathered to a particular ID/AST panel 30. Each data accumulation cycle (i.e., one rotation of the assembly 51), the control processor 70 expects to receive data related to the barcode labels of each ID/AST panels 30 in assembly 51 and test data for each ID/AST panel 30. If either is received, the control processor 70 determines that an ID/AST panel 30 is logically present in that panel location. However, if both types of data are not received, the control processor 70 discards the data for that accumulation cycle.

Upon the completion of one data accumulation cycle, the control processor 70 receives serially the data from the detector microcontrollers 106. This data is stored in the memory. The control processor 70 then interprets the data from the ID wells 31 (i.e., from the wells associated with the ID portion of the ID/AST panels 30 as discussed below) to produce an organism identification. The control processor 70 also interprets the data from AST wells 31 to produce either MIC results or, via National Committee for Laboratory Standard (NCCLS) guidelines, produces an Susceptible, Intermediate, or Resistant (SIR) result which refers to breakpoint for AST categories. The final results for the ID/AST panels 30 are stored memory and may be downloaded to a floppy disk, for example, to conserve storage space within the memory.

Other functions performed by the control processor 70 include communicating with externally connected network devices (e.g., a local area network (LAN) and the like), providing a printer port, performing start-up and diagnostic-self tests to ensure that the instrument 20 is operating properly, and generating appropriate alarm signals. The control processor 70 also provides the operator with a graphical-user interface (not shown) via the instrument front panel 71, and accepts user commands and input via the keyboard 72.

Returning to FIGS. 3A–3C, the ID/AST panels 30 are supplied in a combination format. Each ID/AST panel 30 has reagent well positions capable of performing ID and AST testing on the same panel. As discussed above, the ID/AST panels 30 include the wells 31 and the barcode labels. The wells 31 are segregated into an ID section 33 and an AST section 34. The ID section 33 of the ID/AST panel 30 consists of fifty-one wells 31. The AST section 34 of the ID/AST panel 30 consists of eight-five wells 31. For example, the wells 31 of the AST section 34 may contain dried antibiotics therein.

The ID/AST panels 30 also includes a base 35, a chassis 36, a lid 37, and a cellulose acetate pad 38. Each ID/AST panel 30 also includes a panel label (not shown) which includes information to identify the complete manufacturing history of the particular ID/AST panel 30.

The barcode label provides information related to the ID/AST panel type and also has a unique sequence number for identification purposes. The barcode label can be provided in Code 128, numeric format or any other suitable barcode format.

Each ID/AST panel 30 is inoculated with a broth-suspended organism before being placed into the instrument 20. In practice, the microorganism is a processed and resuspended dilution of microbiological growth from primary culture in either an ID inoculum fluid or an AST inoculum fluid which is then poured into the test panel. The ID/AST panels 30 are inclined with the inoculation ports 39 at the top for filling. Separate inocula are added manually to the ID and AST ports 39. Each well 31 in the ID section 33 is inoculated with the ID inoculum fluid as the inoculum flows down the panel toward the pad 38. Each well 31 in the AST section 34 is inoculated with the AST inoculum fluid. The inocula flow down the ID/AST panel 30 in a serpentine fashion, filling the wells 31 as the liquid front progresses toward the pad 38. Each well 31 is vented, permitting liquid to fill the well 31. Each well 31 has a sharp, circular rim to separate a consistent quantity of liquid from the excess and to isolate each well 31 from liquid in adjacent wells 31. The pad 38 absorbs excess liquid.

The ID/AST panels 30 are inoculated with the inoculum fluids at a panel inoculation station (not shown). Each station holds two tubes of inoculum fluid (i.e., the ID inoculum fluid and the AST inoculum fluid) and supports one ID/AST panel 30. Gravity drives the inoculum fluids through the ID/AST panels 30.

The ID inoculum fluid and AST inoculum fluid comprise the reagent subsystem which includes all reagents required to process isolated bacterial colonies into prepared inocula for addition to the ID section 33 and the AST section 34 of the ID/AST panels 30.

The ID inoculum fluid is used for organism identification. A variety of ID inoculum fluids can be used, although a saline solution is preferred. A detergent may be added to enhance ID/AST panel 30 filling in the panel inoculation station. Preferably, the inoculum density for ID panel inoculation is at least $1\times10^5$ cfu/ml. A variety of identification reagents may be used which include Phenol Red and Iodo-Nitro-Tetrazolium (INT). A variety of substrates may also be used which include 4-Methyl Umbelliferrone (4-MU) derivatives, Methyl-Amino-Coumarin (4-AMC) derivatives, para-Nitrophenol derivatives, and Esculin.

The AST inoculum fluid used for AST determination is a modified formulation of Mueller-Hinton broth. Preferably, the inoculum density for AST panel inoculation is at least $1\times10^5$ cfu/ml. Different inoculum densities may be used for other embodiments of the present invention such as "rapid" AST test results.

These are AST test results obtained within sixteen hours of ID/AST panel 30 inoculation.

A variety of AST indicators may be used. The preferred indicator for AST determinations in the present invention is alamarBlue™, a redox-buffered oxidation-reduction indicator. The indicator is added to the AST inoculum fluid and mixed just prior to addition of the microorganism sample to be tested by the instrument 20.

As mentioned above, the control processor 70 interprets the data from the wells 31 for the purpose of detection, identification and susceptibility testing. The control processor uses three variable threshold levels to interpret this data: an absolute, a dynamic and relative threshold. When using the absolute threshold, a positivity assessment made by determining if the normalized well 31 reading is above (positive) or below (negative) a given predetermined value. When using the dynamic threshold, a reagent reaction determination is calculated using first- and second-differences or other mathematical manipulations of detection data related to the rate-of-change of signal increase as a function of time by determining when certain parameters of the calculated first- and/or second-differences have been exceeded. When using the relative threshold, a reagent reaction determination is made by setting a threshold a predetermined percentage above the starting signal level of the well 31 in question.

In operation, the ID/AST panels 30 are mounted and incubated in the carousel 50 of the instrument 20. As the visible light source assembly 80 and the UV light source assembly 81 are energized sequentially, one reading is taken corresponding to the red, green, blue and fluorescent wavelengths of light. Based on the rotation speed of the carousel 50, light intensity readings are taken at predetermined intervals by the optical measurement system 100.

For example, when the carousel 50 is driven by the drive system 56 at an angular velocity of 2.0 revolutions per minute (RPM), one rotation of the carousel 50 requires 30 seconds. Thus, to accumulate data for red, green, blue and UV wavelengths, two minutes are required. Accordingly, in this example, a complete set of data can be taken by the present invention every two minutes, Since it is possible to vary the angular velocity, different angular velocity may be used for different tests. For example, it may be desirable to accumulate UV data at 1.0 RPM (while other test data is accumulated at 2.0 RPM). In this case, a complete data set would require two and a half minutes to complete.

In the present invention, AST end-point results based on the well 31 readings can be obtained after 18–24 hours of incubation. In an alterative embodiment, AST results can be obtained within 16 hours of panel inoculation.

With regard to identification accuracy, the control processor 70 includes an ID taxa database that includes greater than 126 species for gram-negative organisms, and 103 species for gram-positive organisms. The control processor 70 also includes an AST taxa database equivalent to the ID taxa database for both gram-positive and -negatives. For the purposes of AST testing, the present invention also includes a database with all human and veterinary antimicrobics currently known. As shown in FIG. 16, a plurality of optical filters 87(*a*) and 87(*b*) are disposed between the test panel 30 and the light detection unit 100. The filters 87(*a*) and 87(*b*) pass only light emitted from, or absorbed by, the wells (shown as element 31 in FIG. 3B) having a predetermined bandwidth about a predetermined wavelength.

As shown in FIG. 17, the light detection unit 100 is disposed at a reflection angle to the light source 81. Test panel 30 is positioned opposing the light source 81 and the light detection unit 100 in a reflective manner. The light detection unit 100 detects the light reflected from, or absorbed by, the wells (shown as element 31 in FIG. 3B) of test panel 30. The carousel assembly rotates continuously during testing to position each of the test panels 30 to permit light reflected from, or absorbed by, the wells of the test panel 30 to be detected by the light detection unit 100 as the test panel 30 moves past the light source 81.

While the present invention has been described above in terms of specific embodiments, it is to be understood that the invention is not intended to be confined or limited to the embodiments disclosed herein. On the contrary, the present invention is intended to cover various methods, structures and modifications thereof included within the spirit and scope of the appended claims.

What is claimed is:

1. A diagnostic microbiological testing apparatus, comprising:

a carousel assembly adapted to mount a plurality of test panels each having a plurality of wells for receiving a test inoculum fluid for producing a reaction;

a plurality of light sources capable of directing light of predetermined wavelengths toward the wells of the test panels to cause the wells to emit or absorb light based on the reaction of the test inoculum fluid;

a light detection unit disposed opposing said light sources, with at least one test panel being positioned between said light sources and said light detection unit, said light detection unit for detecting the light emitted from, or absorbed by, the wells of the at least one test panel, wherein said carousel assembly rotates continuously during testing to position each of the test panels between said light sources and said light detection unit to permit light emitted from, or absorbed by, the wells of the test panels to be detected by said light detection unit as the test panels move past said light sources; and a controller adapted to receive a plurality of signals generated by said light detection unit, each signal respectively corresponding to the light detected from a respective well, said controller for determining a test result for each well based on the respective signal.

2. An apparatus according to claim 1, wherein the inoculum fluid comprises one or more reagents and a microbiological test sample.

3. An apparatus according to claim 2, wherein the inoculum fluid produces a reaction for providing an identification test result.

4. An apparatus according to claim 2, wherein the inoculum fluid produces a reaction for providing an antibiotic susceptibility test result.

5. An apparatus according to claim 1, wherein said light sources are arranged to be proximate to each test panel rotated between said light sources and said light detection unit.

6. An apparatus according to claim 1, wherein said light detection unit includes a linear CCD array.

7. An apparatus according to claim 6, further comprising means for spatially averaging an analog linear CCD signal from said linear CCD array so as to eliminate unwanted optical and electrical artifacts from sample column data of said linear CCD array.

8. An apparatus according to claim 7, wherein said averaging means performs said spatial averaging using partial analog decommutation of pixel intensity of the analog linear CCD signal.

9. An apparatus according to claim 6, wherein the wells of a test panel are arranged in rows and columns, and wherein said linear CCD array is positioned to detect light from a column of wells over a predetermined number of scans, said linear CCD array detecting a portion of light of the column of wells on each scan.

10. An apparatus according to claim 9, wherein said carousel assembly further comprises a stepper motor unit for rotating said carousel assembly, and said stepper motor causes said carousel assembly to rotate continuously during testing.

11. An apparatus according to claim 1, wherein said light detection unit includes a linear CCD array, said light sources are capable of selectably generating monochromatic light and can be selectably energized to produce red, green or blue wavelength light, said carousel assembly is also adapted to mount a normalization panel having a plurality of normalization wells, and the plurality of received signals includes a normalization signal generated by the light detection unit from the light emitted from, or absorbed by, the normalization wells of the normalization panel.

12. An apparatus according to claim 11, wherein the selectably energized monochromatic light provides linear illumination over a column of wells of the normalization panel or the test panels.

13. An apparatus according to claim 10, further comprising means for piecewise adjustment along the column of wells in the normalization panel.

14. An apparatus according to claim 13, further comprising means for illuminating a columns of wells the test panels using an illumination profile, thereby allowing an optical response of each well to be measured with uniform sensitivity for all well locations within each column.

15. An apparatus according to claim 1, wherein carousel assembly is also adapted to mount a normalization panel having a plurality of normalization wells, and the plurality of received signals includes a normalization signal generated by the light detection unit from the light emitted from, or absorbed by, the normalization wells of the normalization panel.

16. An apparatus according to claim 15, wherein said controller normalizes the received signals corresponding to the wells of the test panels using the normalization signal.

17. An apparatus according to claim 1, further comprising a plurality of optical filters, each optical filter disposed between the test panels and said light detection unit for passing therethrough only light emitted from, or absorbed by, the wells having a predetermined bandwidth about a predetermined wavelength.

18. An apparatus according to claim 1, wherein said light sources include a first light source capable of selectably generating monochromatic light and a second light source capable of generating UV light.

19. An apparatus according to claim 18, wherein said first light source comprises a plurality of red LEDs, a plurality of green LEDs and a plurality of blue LEDs, and each plurality of said pluralities of LEDs being selectably energized.

20. An apparatus according to claim 18, wherein said first light source comprises a plurality of LEDs arranged in a predetermined manner.

21. An apparatus according to claim 20, wherein said plurality of LEDs are arranged in a column having a top and a bottom end, and wherein the LEDs are spaced closer together at the top and the bottom ends as compared to the LEDs at a center portion of said column.

22. An apparatus according to claim 1, wherein said light detection unit includes a linear detector array.

23. An apparatus according to claim 1, wherein at least one of said light sources is capable of selectably generating light sufficient to produce an emission fluorescence of the test inoculum fluid.

24. An apparatus according to claim 23, where said light source comprises a UV cold-cathode lamp or a UV hot-cathode lamp.

25. An apparatus according to claim 1, wherein each received signal corresponds to a numerical value indicating the intensity of the light detected from each respective well.

26. An apparatus according to claim 1, further comprising a barcode reader for reading barcode labels respectively affixed to the test panels.

27. An apparatus according to claim 1, wherein said control processor determines the test results using calorimetric or fluorometric received signals, or both.

28. An apparatus according to claim 1, further comprising an incubation unit for heating said test panels.

29. An apparatus according to claim 1, further comprising an enclosure surrounding said carousel assembly for preventing detection of ambient light by said light detection unit.

30. An apparatus according to claim 1, wherein said carousel assembly further comprises a carrier adapted to receive and carry the test panels.

31. An apparatus according to claim 1, wherein the wells of a test panel are arranged in rows and columns, and wherein said light sources direct light toward one of the columns of wells.

32. An apparatus according to claim 1, wherein said carousel assembly further comprises a stepper motor unit for rotating said carousel assembly.

33. An apparatus according to claim 1, wherein the test panels are capable of being mounted on said carousel assembly in multiple tiers.

34. A diagnostic microbiological testing system, comprising:

a diagnostic microbiological testing apparatus according to claim 1;

a station for inoculating the test panels with the test inoculum fluid;

a computer workstation comprising:
　a CPU for additionally processing the test result output from the diagnostic microbiological testing apparatus to the computer workstation; and
　a memory for selectively storing the test result from the diagnostic microbiological testing apparatus and the additionally processed test result.

35. A diagnostic microbiological testing apparatus, comprising:

a carousel assembly adapted to mount a plurality of test panels each having a plurality of wells for receiving a test inoculum fluid for producing a reaction;

at least one light source capable of directing light of a predetermined wavelength toward the wells of the test panels to cause the wells to reflect or absorb light based on the reaction of the test inoculum fluid;

a light detection unit disposed at a reflection angle to said light source, with at least one test panel being positioned opposing said light source and said light detection unit in a reflective manner, said light detection unit for detecting the light reflected from, or absorbed by, the wells of the at least one panel, wherein said carousel assembly rotates continuously during testing to position each of the test panels to permit light reflected from, or absorbed by, the wells of the test panels to be detected by said light detection unit as the test panels move past said light source; and a controller adapted to receive a plurality of signals generated by said light detection unit, each signal respectively corresponding to the light detected from each well, said controller for determining a test result for each well based on the received signals.

* * * * *